United States Patent [19]
Cavadini et al.

[11] Patent Number: 5,968,569
[45] Date of Patent: Oct. 19, 1999

[54] PET FOOD PRODUCT CONTAINING PROBIOTICS

[75] Inventors: Christof Cavadini, Le Mont-Pelerin; Olivier Ballevre, Lausanne, both of Switzerland; Walter Gaier, Honfleur, France

[73] Assignee: Nestec S.A., Vevey, Switzerland

[21] Appl. No.: 08/996,889

[22] Filed: Dec. 23, 1997

[30] Foreign Application Priority Data

Mar. 19, 1997 [EP] European Pat. Off. ............. 97200830
Apr. 9, 1997 [EP] European Pat. Off. ............. 97200047

[51] Int. Cl.$^6$ .................................................. A23L 1/168
[52] U.S. Cl. ........................... 426/61; 426/618; 426/620; 426/623; 426/625; 426/805
[58] Field of Search .............................. 426/61, 618, 620, 426/623, 625, 805

[56] References Cited

U.S. PATENT DOCUMENTS

| | | | |
|---|---|---|---|
| 4,943,437 | 7/1990 | Kvanta et al. | 426/61 |
| 5,006,361 | 4/1991 | Cox | 426/601 |
| 5,283,059 | 2/1994 | Suzuki et al. | 424/93 |

FOREIGN PATENT DOCUMENTS

| | | |
|---|---|---|
| 159891 | 10/1985 | European Pat. Off. . |
| 0 180 743 | 5/1986 | European Pat. Off. . |
| 0 287 699 | 10/1988 | European Pat. Off. . |
| 03251159 | 11/1991 | Japan . |
| 2106043 | 9/1979 | United Kingdom . |
| 9117672 | 11/1991 | WIPO . |
| WO 92 12639 | 8/1992 | WIPO . |
| WO 95/34292 | 12/1995 | WIPO . |
| WO 96/08261 | 3/1996 | WIPO . |

OTHER PUBLICATIONS

Derwent Publication XP 002029125, AN 95–121585, 1994.
Derwent Publication XP 002031486, AN 89–312205, 1989.
Fuller, "Probiotics in man and animals", *Journal of Applied Bacteriology*, vol. 66, 1989, pp. 365–378.

*Primary Examiner*—Chhaya D. Sayala
*Attorney, Agent, or Firm*—Hill & Simpson

[57] ABSTRACT

A dried, ready-to-eat pet food product comprising a gelatinized starch matrix which includes a coating or filling which contains a probiotic micro-organism. The cereal product is in the form of a pet food. The product may be produced by cooking a starch source to form a gelatinized starch matrix; forming the gelatinized matrix into pieces; drying the pieces; and coating or filling the pieces with a carrier which contains probiotic micro-organisms.

17 Claims, 1 Drawing Sheet

PET FOOD PRODUCT CONTAINING PROBIOTICS

FIELD OF THE INVENTION

This invention relates to a ready-to-eat cereal product which contains a probiotic micro-organism; for example pet foods, breakfast cereals, infant cereals or convenience foods. In use, the cereal product has a beneficial effect in the gastro-intestinal tract of the person or animal consuming it and hence upon the person or animal. The invention also relates to a process of producing the cereal product and to methods of promoting beneficial effects in the gastro-intestinal tracts of humans and animals.

BACKGROUND OF THE INVENTION

Probiotic micro-organisms are micro-organisms which beneficially affect a host by improving its intestinal microbial balance (Fuller, R; 1989; *J. Applied Bacteriology*, 66: 365–378). In general, probiotic micro-organisms produce organic acids such as lactic acid and acetic acid which inhibit the growth of pathogenic bacteria such as *Clostridium perfringens* and *Helicobacter pylori*. Consequently, probiotic bacteria are believed to be useful in the treatment and prevention of conditions caused by pathogenic bacteria. Further, probiotic micro-organisms are believed to inhibit the growth and activity of putrefying bacteria and hence the production of toxic amine compounds. It is also believed that probiotic bacteria activate the immune function of the host.

Therefore there is considerable interest in including probiotic micro-organisms into foodstuffs. For example, many fermented milk products which contain probiotic micro-organisms are commercially available. Usually these products are in the form of yogurts and an example is the LC1® yogurt (Société des Produits Nestlé SA). Several infant and follow-up formulas which contain probiotic micro-organisms are also commercially available; for example the BIO NAN® formula (Société des Produits Nestlé SA).

Similarly, for animals, there has been interest in including probiotic micro-organisms into animal feeds. For example, Russian patent 2018313 discloses a powdered, spray-dried animal feed which is based upon milk and which contains certain bifidobacteria and streptococci. The animal feed is aimed primarily at live stock although it is mentioned that the feed may be fed to pets.

However, there are two main issues in incorporating probiotic micro-organisms into foodstuffs. First, the foodstuff must be in a form which is palatable to a consumer. Secondly, the probiotic micro-organism must remain viable during storage. The second issue is particularly problematic for ready-to-eat cereal products. These cereal products, unlike fermented milks, are required to have long storage lives; for example at least a year while the cell counts for many probiotic micro-organisms may fall away completely within one or two days. This is particularly the case if the water activity of the foodstuff is above about 0.5. This is usually the case for dried pet foods.

Therefore there is a need for a ready-to-eat cereal product which contains a probiotic micro-organism, is highly palatable, and which is storage stable.

SUMMARY OF THE INVENTION

Accordingly, in one aspect, this invention provides a dried, ready-to-eat cereal product comprising a gelatinized starch matrix which includes a coating or filling containing a probiotic micro-organism.

It has been found that probiotic micro-organisms remain viable for extended periods of time when formulated into a coating on or filling in a dried cereal product. This is surprising since probiotic micro-organisms ordinarily die off rapidly. This is particularly the case for dried, cooked pet foods which generally have a water activity of above about 0.5; levels at which probiotic micro-organisms ordinarily die off rapidly. Therefore the invention offers the advantage of a ready-to-eat cereal product which is highly palatable and which contains a shelf stable source of probiotic micro-organisms.

The cereal product may be in the form of a dried pet food, breakfast cereal, an infant cereal, or a convenience food such as a cereal bar. For human foods, the gelatinized starch matrix is preferably in flaked or expanded form. For pet foods, the gelatinized starch matrix is preferably in the form of kibbles or pieces. The gelatinized matrix is preferably produced by extrusion cooking a starch source.

Preferably the coating comprises a carrier substrate which carries the probiotic micro-organism in it. The filling may also comprise a carrier substrate which carries the probiotic micro-organism in it. For example, the carrier substrate may be protein digest, fat, milk solids, sugar or a particulate flavoring agent.

In a further aspect, this invention provides a process of preparing a dried, ready-to-eat cereal product, the process comprising cooking a starch source to form a gelatinized starch matrix; forming the gelatinized starch matrix into pieces and drying the pieces; and coating or filling the pieces with a substrate which contains probiotic micro-organisms.

In one embodiment, the gelatinized starch matrix is formed into pieces and dried by extruding the gelatinized matrix to form a cooked extrudate and cutting and drying the cooked extrudate to form dried pieces. The gelatinized matrix may be caused to expand upon extrusion to form, after cutting and drying, expanded pieces. Alternatively, the pieces may be subjected to flaking to form flaked pieces.

In another embodiment, the gelatinized starch matrix may be formed into pieces and dried by roller-drying the gelatinized starch matrix to form flakes.

In a further embodiment, the gelatinized starch matrix may be formed into pieces and dried by extruding the gelatinized matrix to form a cooked extrudate containing an aperture; and cutting and drying the pieces. Preferably the gelatinized starch matrix is extruded with a central bore for receiving a filling.

BRIEF DESCRIPTION OF THE DRAWINGS

Embodiments of the invention are now described, by way of example only, with reference to the drawings in which.

DETAILED DESCRIPTION OF PREFERRED EMBODIMENTS OF THE INVENTION

Embodiments of the invention are now described, by way of example only. The invention provides a dried, ready-to-eat cereal product in the form of a gelatinized starch matrix which includes a coating or filling. The coating or filling contains a probiotic micro-organism. The probiotic micro-organism may be selected from one or more micro-organisms suitable for human or animal consumption and which is able to improve the microbial balance in the human or animal intestine.

Examples of suitable probiotic micro-organisms include yeasts such as Saccharomyces, Debaromyces, Candida, Pichia and Torulopsis, moulds such as Aspergillus, Rhizopus, Mucor, and Penicillium and Torulopsis and bacteria such as the genera Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus and Lactobacillus. Specific examples of suitable probiotic micro-organisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus* (Lactobacillus GG), *Lactobacillus sake, Lactococcus lactis, Micrococcus varians, Pediococcus acidilactici, Pediococcus pentosaceus, Pediococcus acidilactici, Pediococcus halophilus, Streptococcusfaecalis, Streptococcus thermophilus, Staphylococcus carnosus,* and *Staphylococcus xylosus*. The probiotic micro-organisms are preferably in powdered, dried form; especially in spore form for micro-organisms which form spores. Further, if desired, the probiotic micro-organism may be encapsulated to further increase the probability of survival; for example in a sugar matrix, fat matrix or polysaccharide matrix.

The dried, ready-to-eat cereal product may be produced from any suitable ingredients; such as those commonly used in dried, ready-to-eat cereal products. One of these ingredients is a starch source. Suitable starch sources are, for example, grain flours such as corn, rice, wheat, beets, barley, soy and oats. Also mixtures of these flours may be used. The flours may be whole flours or may be flours which have had fractions removed; for example the germ fraction or husk fraction may be removed. Rice flour, corn flour and wheat flour are particularly suitable; either alone or in combination. The starch source will be chosen largely on the basis of the nutritional value, palatability considerations, and the type of cereal product desired.

The cereal product may also contain a starch source. Suitable protein sources may be selected from any suitable animal or vegetable protein source; for example meat meal, bone meal, fish meal, soy protein concentrates, milk proteins, gluten, and the like. The choice of the protein source will be largely determined by the nutritional needs, palatability considerations, and the type of cereal product produced. Of course, the starch source may also be a source of protein.

The cereal product may be produced in many different ways as desired. However, an especially suitable way of producing the cereal product is by extrusion cooking. This may be done as is well known in the art. For example, in one suitable process, a feed mixture is fed into a preconditioner. The feed mixture is primarily made up of the starch source and other ingredients such as sugar, salt, spices, seasonings, vitamins, minerals, flavoring agents, coloring agents, antioxidants, protein sources, fats and the like. If desired, sources of insoluble fiber may also be included; for example wheat bran, corn bran, rice bran, rye bran and the like. Further, if desired, a source of soluble fiber may be included, for example, chicory fibers, inulin, fructooligosaccharides, soy oligosaccharides, oat bran concentrate, guar gum, carob bean gum, xantham gum, and the like. Preferably the soluble fiber selected is a substrate for the micro-organism selected, or such that the soluble fiber and micro-organism form a symbiotic relationship for promoting beneficial effects. The maximum level of soluble fiber is preferably about 20% by weight; especially about 10% by weight. For example, for pet foods, chicory may be included to comprise about 1% to about 20% by weight of the feed mixture; more preferably about 2% to about 10% by weight.

Depending upon the desired form of the cereal product, the starch content of the feed mixture may be varied. For example, for an expanded cereal product, the feed mixture preferably includes up to about 40% by weight of starch. However, for a flaked product, it is not necessary to use large amounts of starch in the feed mixture since it is possible to flake an unexpanded product.

In the preconditioner, water or steam, or both, is mixed into the feed mixture. Sufficient water or steam is mixed into the feed mixture to moisten the feed mixture. If desired, the temperature of the feed mixture may be raised in the preconditioner to about 60° C. to about 90° C. by weight. A suitable preconditioner is described in U.S. Pat. No. 4,752, 139. It is not necessary to subject the feed mixture to preconditioning but it is advantageous to do so.

The moistened feed leaving the preconditioner is then fed into an extruder. The extruder may be any suitable single or twin screw, cooking-extruder. Suitable extruders may be obtained from Wenger Manufacturing Inc, Clextral SA, Bühler AG, and the like. During passage through the extruder, the moistened feed passes through a cooking zone, in which it is subjected to mechanical shear and is heated; for example up to a maximum temperature of up to about 150° C., and a forming zone. The gauge pressure in the forming zone is about 300 kPa to about 10 MPa, as desired. If desired, water or steam, or both, may be introduced into the cooking zone. During passage through the extruder, the starch source of the moistened feed is gelatinized to provide a gelatinized starch matrix.

If desired, a small amount of an edible oil may be fed into the extruder along with the moistened feed to facilitate the extrusion process or as a carrier for oil soluble additives. Any suitable oil may be used; for example vegetable oils such as sunflower oil, safflower oil, corn oil, and the like. If oils are used, oils which are high in mono-unsaturates are particularly preferred. Hydrogenated oils or fats are also preferred. The amount of oil used is preferably kept below about 1% by weight.

The gelatinized matrix leaving the extruder is forced through a suitable die; for example a die as described in European patent application 0665051; the disclosure of which is incorporated by reference. A shaped extrudate, which has a cross-sectional shape corresponding to that of the orifice of the die, leaves the die. If it is desired to produce a center-filled cereal product, the gelatinized matrix may be extruded with a central bore. The shaped extrudate is then cut into pieces using rotating blades at the exit of the die. Depending upon the conditions in the extruder and the composition of the shaped extrudate, the shaped extrudate expands to a greater or lesser extent. In the case of pet foods, little or no expansion usually takes place.

If a flaked product is to be produced, the pieces may then be transferred to a flaking apparatus. Suitable apparatus are well known and widely used in the cereal industry and may be purchased from, for example, Bühler AG in Switzerland. If desired, the pieces may be partially dried before flaking.

The pieces are then dried to a moisture content below about 10% by weight. This is conveniently carried out in a hot air drier as is conventional. For breakfast cereals, moisture contents of about 1% to about 3% by weight are preferred.

The pieces intended for pet foods may be in the form of chewable pieces. The pieces usually have a water activity of about 0.5 to about 0.7.

The expanded pieces intended for human foods have a crispy, pleasant texture and good organoleptic properties. The flaked pieces also have good texture and organoleptic properties. The pieces have a pleasant taste of toasted cereal. Conveniently, the density of the pieces may be less than about 300 g/l. At this point, the expanded or flaked pieces usually have a water activity of about 0.15 to about 0.3.

The probiotic micro-organisms are then mixed into a suitable carrier substrate. The carrier substrate will vary depending on whether the pieces are intended for animals or humans. For pet foods, suitable carrier substrates include animal fats such as tallow, vegetable fats such as hydrogenated soy fat, protein digests which are commonly used as flavor coatings, and water. For human foods, suitable carrier substrates include liquids, such as fats and sugar solutions, and particulate coatings such as particulate flavor coatings. Suitable fats are edible vegetable oils and fats; for example hydrogenated soy fat. Suitable particulate flavor coatings include sugars, chocolate powders, milk powders, malted powders, flavored beverage powders, and the like. If desired, the probiotic micro-organisms may be encapsulated.

Protection agents to improve the survival of the micro-organisms may be incorporated into the carrier substrate. Examples of suitable protecting agents are vitamins such as vitamins C and E, amino acids and their salts such as lysine, glycine, cysteine and sodium glutamate, sugars such as lactose, trehalose, saccharose, dextrin and maltodextrin, and proteins such as milk and soy proteins. Trace elements and minerals may also be included in the carrier substrate.

The selection of the carrier substrate will depend upon factors such as palatability considerations and the survival of the probiotic micro-organism since some micro-organisms survive better in some carrier substrates than others. For example, it is found that *S. cereviseae* may be slightly less stable in protein digests than in fats. If fats are used in the carrier substrate, the carrier substrate preferably contains antioxidants to reduce the action of oxygen on sensitive micro-organisms. However selecting the optimum carrier substrate is a matter of simple trial and error for the skilled person. If necessary, the carrier substrate may be heated slightly to melt it or to reduce its viscosity.

To produce a coated cereal product, any technique suitable for coating the pieces may be used. For example, in the case of a liquid carrier substrate, the mixture of the probiotic micro-organism and the carrier substrate may be sprayed onto the dried pieces. This may be carried out in any suitable manner. For example, the pieces may be fed into a fluidized bed onto which the mixture is sprayed. Alternatively, the pieces may be fed into a rotary coater into which the mixture is sprayed. As a further alternative, the pieces may be caused to fall in a curtain and the coating mixture sprayed onto the curtain. In the case of a particulate carrier substrate, the probiotic micro-organism and the carrier substrate may be mixed to form a dry mix. Heat sensitive components such as vitamins, amino acids, etc may also be included in the dry mix. The dry mix is then agglomerated on the dried pieces using an agglomerating agent. A suitable procedure is described in U.S. Pat. No. 4,777,056; the disclosure of which is incorporated by reference. Fats, oils and sugar solutions are examples of suitable agglomerating agents. Particulate carrier substrates may also be dusted onto the cereal product.

For a filled cereal product, the mixture of the probiotic and micro-organism and carrier substrate is filled into the central bore of each piece. In this case, the carrier substrate is preferably viscous or a substance which hardens rapidly. Fats are particularly suitable. Alternatively the cereal product and carrier substrate may be fed into a tumbler and the carrier substrate agglomerated to the cereal product using a syrup. In this case, the cereal product is coated and filled.

The dried, ready-to-eat cereal product conveniently contains about $10^4$ to about $10^{10}$ cells of the probiotic micro-organism per gram of the dried cereal product; preferably about $10^6$ to about $10^8$ cells of the probiotic micro-organism per gram. The dried cereal product may contain about 0.5% to about 20% by weight of the mixture of the probiotic micro-organism and carrier substrate; preferably about 1% to about 6% by weight; for example about 3% to about 6% by weight.

The dried cereal product may then be further processed as desired. For example, if the dried cereal is to be used as a breakfast cereal, dried fruit, nuts, other cereals, dried milk produce (such as dried yogurt etc) may be dry mixed with or agglomerated with the coated cereal. If desired, the dried cereal may be further coated with protective agents or flavoring agents, or both. This may also be carried out prior to or during coating or filling of the dried pieces with the mixture of the probiotic and micro-organism and carrier substrate.

It is also possible to produce a dried cereal product by mixing together water and the ingredients of cereal product; for example in a preconditioner. The wet mixture may then be shaped into a desired shape; for example using shaping rollers. The shaped mixture may then be baked in an oven; for example at about 220° C. to about 280° C. for about 10 minutes to about 1 hour. The dried cereal product has the appearance of a baked biscuit. The coating or filling may then be applied as discussed above.

Alternatively the cereal product may be formulated into convenience foods such as snack bars and the like. Again the cereal product may be mixed with nuts, dried fruit, sugars or other sweeteners, coloring agents, or flavoring agents, and the like. A suitable binder, for example arabic gum or gelatin, may then be added. An agent which reduces breakability of the bar may also be included; for example hydrolyzed wheat. If desired, the bar may be coated with a suitable coating; for example chocolate. Processes for manufacturing snack bars are well known and are described in the art; see for example U.S. Pat. No. 4,871,557.

It will be appreciated that the dried, ready-to-eat cereal product may be produced by any suitable process and not only that described above.

In the case of human foods, the dried, ready-to-eat cereal product preferably comprises a nutritional supplement. In the case of pet foods, the dried, ready-to-eat cereal product may be fed to pets as a sole source of nutrition or may be supplemented by other sources of nutrition; for example canned food. When consumed in adequate amounts, the dried, ready-to-eat cereal product results in a production of acids, such as lactic acid and acetic acid, in the gut of the human or animal. This inhibits the growth of pathogenic bacteria such as *Clostridium perfringens* or those which adversely affect well being, and has a beneficial effect on the human or animal. Also, the probiotic micro-organisms adhere to intestinal surfaces and compete with undesired bacteria. Further, the growth and activity of putrefying bacteria may be inhibited and hence the production of toxic amine compounds. Adequate amounts of the dried, ready-to-eat cereal product may also result in the activation of the immune function of the human or animal.

The amount of the dried, ready-to-eat cereal product to be consumed by the human or animal to obtain a beneficial effect will depend upon the size and age of the human or animal. However an amount of the dried, ready-to-eat cereal product to provide a daily amount of about $10^6$ to about $10^{12}$ cells of the probiotic micro-organism would usually be adequate.

Numerous modifications may be made to the embodiments described above. For example, it is not necessary to produce the cereal product by extrusion cooking. Instead the cereal product may be produced by any suitable method of producing dried, ready-to-eat cereal pieces. For example, the feed materials may be cooked with water to provided a cooked paste. The paste is then roller-dried to produce dried flakes; usually of a thickness of about 0.6 to about 1 mm.

Specific examples are now described for further illustration.

EXAMPLE 1

A feed mixture is made up of corn, corn gluten, chicken and fish meal, salts, vitamins and minerals. The feed mixture is fed into a preconditioner and moistened. The moistened feed leaving the preconditioner is then fed into an extruder-cooker and gelatinized. The gelatinized matrix leaving the extruder is forced through a die and extruded. The extrudate leaving the die head is cut into pieces suitable for feeding to dogs, dried at about 110° C. for about 20 minutes, and cooled to form pellets. The water activity of the pellets is about 0.6.

The pellets sprayed with three different coating mixtures. Each coating mixture contains *Bacillus coagulans* but one coating mixture uses hydrogenated soy fat as a coating substrate, one coating mixture uses water as a coating substrate, and one coating mixture uses a protein digest as a coating substrate. The *B. coagulans* is in the form of powdered endospores and is obtainable from Sankyo Pharmaceutical Company under the trade name Lacris-S. The pellets contain about $1.6 \times 10^6$ cells/g of *B. coagulans*. For each coating mixture, the pellets are separated into two groups. One group is stored at about 25° C. and, to estimate the long term stability of the micro-organism, the other group is stored at about 37° C. A sample is taken of each group is taken after 1 week, 2 weeks, 3 weeks and 4 weeks. Also, a fat coated sample of the group which is stored at 37° C. is taken at 8 weeks.

Figure 1:
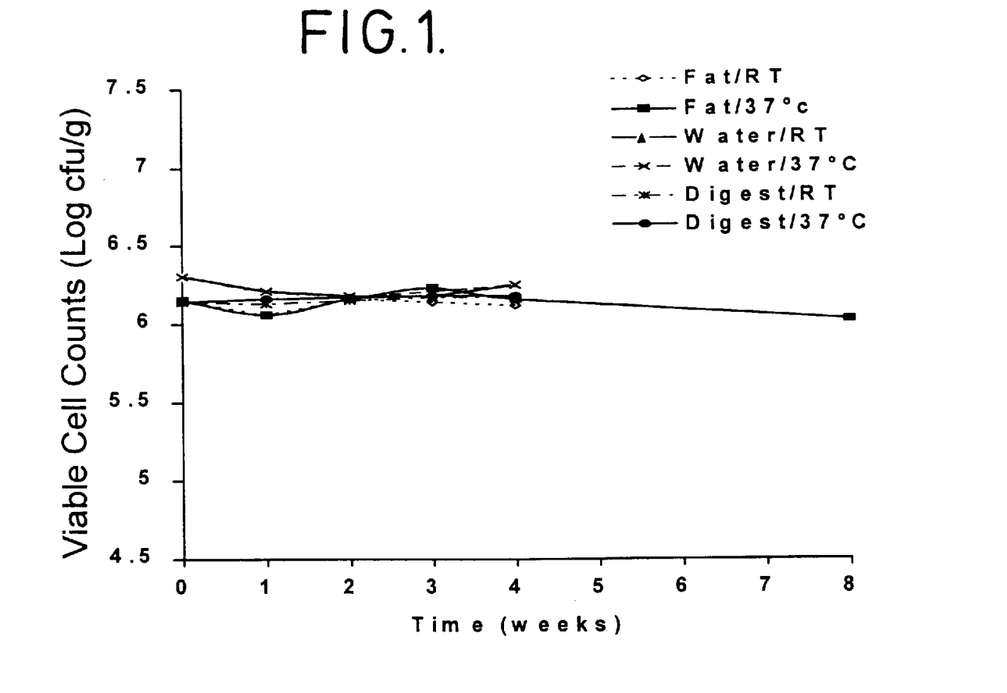
FIG. 1 is a graph illustrating the viability of *Bacillus coagulans* in various coatings on a dried, cooked, pet food.

The cell counts are determined for each sample. The results are set out in FIG. 1. In all cases, the cell counts remain substantially constant indicating excellent storage stability. Further, the results from the storage at 37° C. for 8 weeks indicate that the micro-organisms are likely to be stable after one year of storage at normal conditions.

EXAMPLE 2

Example 1 is repeated except that the three different coating mixtures each contain *Bacillus subtilis* instead of *Bacillus coagulans*. The *B. subtilis* is in the form of powdered endospores and is obtainable from Hansen A/S under the trade name BioPlus 2B. The results are set out in FIG. 2.

Figure 2:
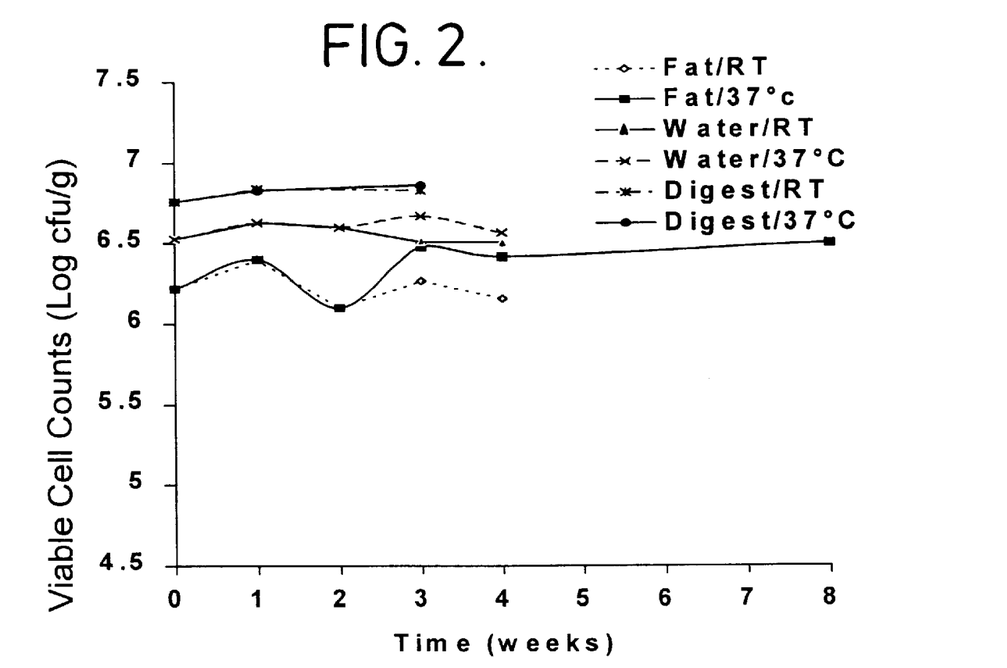
FIG. 2 is a graph illustrating the viability of *Bacillus subtilis* in various coatings on a dried, cooked, pet food.

In all cases, the cell counts remain substantially constant indicating excellent storage stability. However the cell counts for the pellets coated with fat are a little lower than those for water and protein digest but are still substantially constant. Again the results from the storage at 37° C. for 8 weeks indicate that the micro-organisms are likely to be stable after one year of storage at normal conditions.

EXAMPLE 3

Example 1 is repeated except that the three different coating mixtures each contain *Pediococcus acidilactici* instead of *Bacillus coagulans*. The *P. acidilactici* is in the form of a dried powder and is obtainable from Lallmand SA under the trade name Bactocell. The storage results are as follows:

| Weeks | Fat 25° C. | Fat 37° C. | Water 25° C. | Water 37° C. | Digest 25° C. | Digest 37° C. |
| --- | --- | --- | --- | --- | --- | --- |
| 0 | $19.6 \times 10^6$ | $19.6 \times 10^6$ | $21.9 \times 10^6$ | $21.9 \times 10^6$ | $12.9 \times 10^6$ | $12.9 \times 10^6$ |
| 1 | $13.6 \times 10^6$ | $13.6 \times 10^6$ | $14.7 \times 10^6$ | $14.7 \times 10^6$ | $12.1 \times 10^6$ | $2.93 \times 10^6$ |
| 2 | $12.9 \times 10^6$ | $12.9 \times 10^6$ | $13.1 \times 10^6$ | $13.1 \times 10^6$ | — | — |
| 3 | $9.73 \times 10^6$ | $6.69 \times 10^6$ | $16.0 \times 10^6$ | $6.07 \times 10^6$ | $7.77 \times 10^6$ | $0.76 \times 10^6$ |
| 4 | $12.9 \times 10^6$ | $4.6 \times 10^6$ | $14.0 \times 10^6$ | $5.31 \times 10^6$ | — | — |
| 5 | — | — | — | — | $5.1 \times 10^6$ | $0.68 \times 10^6$ |
| 8 | $6.8 \times 10^6$ | $1.5 \times 10^6$ | — | — | — |

For the pellets coated using water or fats, the cell counts remain substantially constant at about $10^7$ cfu/g; indicating excellent storage stability. For the pellets coated using protein digest, when stored at 37° C., the cell counts initially fall off but then stabilize at about $10^6$ cfu/g; which is adequate.

EXAMPLE 4

Example 1 is repeated except that the three different coating mixtures each contain *Saccharomyces cereviseae* instead of *Bacillus coagulans*. The *S. cereviseae* is in the form of a dried powder and is obtainable from Santel SA under the trade name Levucell. The storage results are as follows:

| Weeks | Fat 25° C. | Fat 37° C. | Water 25° C. | Water 37° C. | Digest 25° C. | Digest 37° C. |
| --- | --- | --- | --- | --- | --- | --- |
| 0 | $28.0 \times 10^6$ | $28.0 \times 10^6$ | $27.6 \times 10^6$ | $27.6 \times 10^6$ | $11.3 \times 10^6$ | $11.3 \times 10^6$ |
| 1 | $23.2 \times 10^6$ | $23.3 \times 10^6$ | $17.2 \times 10^6$ | $17.2 \times 10^6$ | $7.53 \times 10^6$ | $1.83 \times 10^6$ |
| 2 | $24.5 \times 10^6$ | $24.5 \times 10^6$ | $18.7 \times 10^6$ | $18.7 \times 10^6$ | — | — |
| 3 | $24.5 \times 10^6$ | $9.93 \times 10^6$ | $13.5 \times 10^6$ | $4.40 \times 10^6$ | $1.99 \times 10^6$ | $0.16 \times 10^6$ |

-continued

| Weeks | Fat 25° C. | Fat 37° C. | Water 25° C. | Water 37° C. | Digest 25° C. | Digest 37° C. |
|---|---|---|---|---|---|---|
| 4 | $13.7 \times 10^6$ | $15.9 \times 10^6$ | — | — | — | — |
| 5 | — | — | — | — | $2.42 \times 10^6$ | $0.03 \times 10^6$ |
| 8 | $17.5 \times 10^6$ | $12.3 \times 10^6$ | — | — | — | — |

For the pellets coated using water or fats, the cell counts remain substantially constant at about $10^7$ cfu/g; indicating excellent storage stability. This is particularly the case for the pellets coated with fats However the cell counts for the pellets coated with protein digest are a little lower than those for water and fat but are still acceptable when stored at 25° C. When stored at 37° C., the cell counts for the pellets coated with protein digest fall off.

EXAMPLE 5

A trial is conducted using 30 dogs. The dogs are fed a standard dried diet for a week prior to commencement of the trials. Immediately prior to commencement of the trials, the gut flora and a measure of the fecal odors for each dog is determined.

The dogs are then separated into two groups of 15 dogs. One group of dogs is fed the dried, fat coated pellets of example 1. The other group of dogs is fed the same pellets but without the coating of fat and probiotic micro-organism. The dogs are given free access to the food and to water.

After a week, the gut flora of each dog is analyzed. The dogs which are fed the pellets of example 1 have decreased counts of *C. perfringens*. Further, fecal pH and odors are found to have decreased in the dogs which are fed the pellets of example 1.

EXAMPLE 6

A feed mixture is made up of 70% by weight of corn flour, 17% by weight of wheat flour, 7% by weight sugar, 3% by weight of malt, 2% by weight of vegetable fats, and salt. The feed mixture is fed into a preconditioner and moistened. The moistened feed leaving the preconditioner is then fed into an extruder and gelatinized. The gelatinized matrix leaving the extruder is forced through a die and extruded. The extrudate expands upon leaving the die head and is cut into pieces of about 1 cm. The pieces are then dried to a moisture content of about 1% by weight.

The pieces are sprayed with two different coating mixtures. Each coating mixture contains sunflower oil as the carrier substrate but a different micro-organism. The micro-organisms are:

| Micro-organism | Source | Form |
|---|---|---|
| Saccharomyces cereviseae | Santel SA (Levucell ™) | Spray dried powder |
| Enterococcus faecium SF68 | Bioferment Division of Cerbios Pharma SA (LBC-K ™), Switzerland | Spray dried powder |

Both micro-organisms are commercially available. The pieces all contain about $10^6$ cells/g to $10^7$ cells/g of the probiotic micro-organism. To obtain an idea of the long term stability of the micro-organism, the pieces are stored at about 37° C. A sample of each group is taken immediately after production, after 1 week and 3 weeks.

The viable cell counts are determined for each sample. The results are as follows:

| Micro-organism | Cell count- Day 1 (cells/g) | Cell count- 1 week (cells/g) | Cell count- 3 weeks (cells/g) |
|---|---|---|---|
| Saccharomyces cereviseae | $6.40 \times 10^6$ | $2.21 \times 10^6$ | $3.90 \times 10^6$ |
| Enterococcus faecium SF68 | $1.38 \times 10^6$ | $8.60 \times 10^6$ | $4.03 \times 10^6$ |

The results indicate that the probiotic micro-organisms remain substantially stable.

EXAMPLE 7

The procedure of example 6 is repeated except that the coating mixture is a dry mix of the probiotic micro-organisms and chocolate-flavored powder (Nesquik® powder). The dry mix is coated on the pieces using the procedure described in U.S. Pat. No. 4,777,056 and using vegetable oil as an agglomerating agent.

Further, the following micro-organisms are used:

| Micro-organism | Source | Form |
|---|---|---|
| B. coagulans | Sankyo Pharmaceutical Company (Lacris-S ™), Japan | Powdered endospores |
| L. johnsonii La1 | Nestec SA | Freeze dried powder |
| Bifidobacterium animalis/longum | Ch. Hansen A/S (Bb12 ™), Denmark | Freeze dried powder |
| Saccharomyces cereviseae | Santel SA (Levucell ™) | Spray dried powder |
| Enterococcus faecium SF68 | Bioferment Division of Cerbios Pharma SA (LBC-K ™), Switzerland | Spray dried powder |

The first, third, fourth and fifth micro-organisms are commercially available. The second micro-organism is described in EP 0577904 and was deposited at the Collection Nationale de Cultures de Microorganismes (CNCM), Institut Pasteur, 28 rue du Dr Roux, 757724 Paris Cedex 15, France on Jun. 30 1992 under the number CNCM I-1225 and name La 1 by Société des Produits Nestlé S.A.

The cell counts determined for each sample. The results are as follows:

| Micro-organism | Cell count- Day 1 (cells/g) | Cell count- 1 week (cells/g) | Cell count- 3 weeks (cells/g) |
|---|---|---|---|
| B. coagulans | $6.37 \times 10^6$ | $5.07 \times 10^6$ | $4.24 \times 10^6$ |
| L. johnsonii La1 | $1.43 \times 10^6$ | $3.21 \times 10^5$ | $1.39 \times 10^5$ |
| Bifidobacterium animalis/longum | $8.06 \times 10^6$ | $2.95 \times 10^6$ | $9.80 \times 10^5$ |
| Saccharomyces cereviseae | $2.43 \times 10^5$ | $2.17 \times 10^5$ | $1.38 \times 10^5$ |
| Enterococcus faecium SF68 | $1.94 \times 10^6$ | $5.70 \times 10^5$ | $1.50 \times 10^4$ |

The results indicate that the *B. coagulans* and *Bifidobacterium animalis*/longum are likely to remain stable for long periods. The other micro-organisms display less but acceptable stability.

EXAMPLE 8

Expanded cereal products produced as described in example 6 are coated with three coating substrates. Product 1 is prepared by coating the cereal product with vegetable oil and then dusting on a spray-dried milk powder which contains *L. johnsonii* La1; Product 2 is prepared by coating the cereal product with vegetable oil and then dusting on a mixture of a spray-dried milk powder which contains *L. johnsonii* La1 and a cocoa-containing powder (Nesquik® powder); Product 3 is prepared by suspending a spray-dried milk powder which contains *L. johnsonii* La1 in a vegetable oil and spraying the oil (without pressure) on the cereal product.

The cell counts determined for each product. The results are as follows:

| Product | Cell count-<br>Day 1 (cells/g) | Cell count-<br>1 week (cells/g) | Cell count-<br>3 weeks (cells/g) |
|---|---|---|---|
| 1 | $3.86 \times 10^7$ | $4.42 \times 10^7$ | $3.00 \times 10^7$ |
| 2 | $1.59 \times 10^7$ | $2.30 \times 10^7$ | $1.65 \times 10^7$ |
| 3 | $3.51 \times 10^7$ | $4.61 \times 10^6$ | $3.36 \times 10^6$ |

The results indicate that the probiotic micro-organisms remain substantially stable.

EXAMPLE 9

A trial is conducted using 20 adult volunteers. Immediately prior to commencement of the trials, the gut flora of each volunteer is determined. The volunteers are then separated into two groups of 10 people. One group is fed, for breakfast, a 30 g portion of product 1 of example 8 along with cold milk. The other group is fed the same cereal product but without the coating of fat and probiotic micro-organism. Other meals during the day are the normal meals eaten by the volunteers.

After a week, the gut flora of each volunteer is analyzed. The volunteer which are fed Product 1 have decreased counts of C.

We claim:

1. A dried, ready-to-eat pet food kibble comprising:
   a gelatinized starch matrix;
   a lipid coating around the gelatinized starch matrix, the lipid coating including a probiotic micro-organism; and
   a flavor coating including a protein digest.

2. A pet kibble according to claim 1 in which the gelatinized matrix is an extrusion cooked starch source.

3. A pet kibble according to claim 1 in which the coating comprises a carrier substrate which contains the probiotic micro-organism.

4. A pet kibble according to claim 3 in which the carrier substrate is at least one carrier chosen from the group consisting of a fat, a protein digest, milk solids, a sugar and a particulate flavoring agent.

5. A pet kibble according to claim 1 in which the probiotic micro-organism is selected from the group consisting of *Bacillus coagulans, Bacillus licheniformis, Bacillus subtilis, Bifidobacterium animalis/longum, L. johnsonii* La1, *Pediococcus acidilactici, Saccharomyces cereviseae*, and *Enterococcus faecium* SF68.

6. A pet kibble according to claim 1 further containing a source of soluble fiber.

7. A dried, ready-to-eat pet food in the form of kibbles, each kibble comprising:
   a gelatinized starch matrix which includes a protein source,
   a coating or a filling containing a probiotic micro-organism.

8. A pet food product according to claim 7 in which the coating or filling comprises a carrier substrate which contains the probiotic micro-organism.

9. A pet food product according to claim 8 in which the carrier substrate is a fat, or a protein digest, or a mixture thereof.

10. A pet food product according to claim 7 in which the probiotic micro-organism is selected from *Bacillus coagulans, Bacillus licheniformis, Bacillus subtilis*, Bifidobacterium sp., *Pediococcus acidilactici, Saccharomyces cereviseae*, and *Enterococcus faecium* SF68.

11. A pet food product according to claim 7 further containing a source of soluble fiber.

12. A dried, ready-to-eat pet food in the form of coated kibbles, each kibble comprising:
   a gelatinized starch matrix which includes a protein source,
   a coating of a carrier substrate which contains a probiotic micro-organism; the carrier substance being a fat, or a protein digest, or a mixture thereof.

13. A pet food product according to claim 12 in which the probiotic micro-organism is selected from *Bacillus coagulans, Bacillus licheniformis, Bacillus subtilis*, Bifidobacterium sp., *Pediococcus acidilactici, Saccharomyces cereviseae*, and *Enterococcus faecium* SF68.

14. A pet food product according to claim 12 further containing a source of soluble fiber.

15. A process of preparing a dried, ready-to-eat pet food, the process comprising cooking a starch source and a protein source to form a gelatinized starch matrix containing protein; forming the gelatinized matrix into kibbles; drying the kibbles; and coating the kibbles with a coating which contains probiotic micro-organisms.

16. A process according to claim 15 in which the starch source and protein source are extrusion cooked; extruded through an orifice; and then cut into kibbles.

17. A dried, ready-to-eat pet food kibble comprising:
   a gelatinized starch matrix which includes a component chosen from the group consisting of inulin and fructooligosaccharides;
   a coating containing a probiotic micro-organism.

* * * * *

(12) EX PARTE REEXAMINATION CERTIFICATE (7636th)
United States Patent
Cavadini et al.

(10) Number: US 5,968,569 C1
(45) Certificate Issued: Jul. 27, 2010

(54) PET FOOD PRODUCT CONTAINING PROBIOTICS

(75) Inventors: Christof Cavadini, Le Mont-Pelerin (CH); Olivier Ballevre, Lausanne (CH); Walter Gaier, Honfleur (FR)

(73) Assignee: Nestec S.A., Vevey (CH)

Reexamination Request:
No. 90/009,415, Apr. 9, 2009

Reexamination Certificate for:
| | |
|---|---|
| Patent No.: | 5,968,569 |
| Issued: | Oct. 19, 1999 |
| Appl. No.: | 08/996,889 |
| Filed: | Dec. 23, 1997 |

(30) Foreign Application Priority Data

| Mar. 19, 1997 | (EP) | ............................................. 97200830 |
|---|---|---|
| Apr. 9, 1997 | (EP) | ............................................. 97200047 |

(51) Int. Cl.
| | |
|---|---|
| *A23L 1/03* | (2006.01) |
| *A23L 1/164* | (2006.01) |
| *A23L 1/18* | (2006.01) |
| *A23K 1/18* | (2006.01) |
| *A23K 1/00* | (2006.01) |
| *A23L 1/168* | (2006.01) |

(52) U.S. Cl. .......................... 426/61; 426/618; 426/623; 426/805; 426/625; 426/620

(58) Field of Classification Search ........................ None
See application file for complete search history.

(56) References Cited

U.S. PATENT DOCUMENTS

| | | | |
|---|---|---|---|
| 2,328,025 A | | 8/1943 | Mead et al. |
| 3,962,416 A | | 6/1976 | Katzen |
| 3,997,675 A | | 12/1976 | Eichelburg |
| 4,006,266 A | * | 2/1977 | Bone et al. .................. 426/623 |
| 4,518,696 A | | 5/1985 | Gehrman et al. |
| 4,752,139 A | | 6/1988 | Hauck |
| 4,777,056 A | | 10/1988 | Buhler et al. |
| 5,494,664 A | | 2/1996 | Brassart et al. |

FOREIGN PATENT DOCUMENTS

| | | |
|---|---|---|
| EP | 0088574 A1 | 9/1983 |
| EP | 0251630 A2 | 1/1988 |
| EP | 0577904 A1 | 1/1994 |
| EP | 0665051 A1 | 8/1995 |
| GB | 1503094 | 3/1978 |
| JP | 64-039953 | 10/1989 |
| JP | 3251159 | 11/1991 |
| JP | 04-169179 | 6/1992 |
| RU | 2018313 C1 | 8/1994 |
| WO | WO9414342 A1 | 7/1994 |
| WO | WO9631128 A1 | 10/1996 |

OTHER PUBLICATIONS

LR Beuchat, "Water activity and microbial stability" Downloaded from www.wateractivity.org/BeuchatIFT2002.pdf, accessed Feb. 8, 2010.*

Donohue et al., Safety of Probiotic Bacteria, Asia Pacific Journal of Clinical Nutrition, Vo. 5, No. 1, pp. 25–28, 1996.

Eagle Products, Inc. Eagle Stress Pack leaflet, Apr. 1, 1988.

Frame, N.D. (Ed.), The Technology of Extrusion Cooking, Preface and pp. 52–189, 1994.

Fujisawa et al., Taxonomic Study Of The *Lactobacillus Acidophilus* Group, With . . . , International Journal of Systematic Bacteriology, vol. 42, No. 3, pp. 487–491, Jul. 1992.

Lee et al., The Coming of Age of Probiotics, Trends in Food Science and Technology, vol. 6, No. 7, pp. 241–245, Jul. 1995.

Association of American Feed Control Officials (AAFCO), "Feed Ingredient Definitions," Official Publication 1997, pp. 216–221.

FAO Food and Nutrition Paper 85, 2002; "Probiotics in Food—Health and Nutritional Properties and Guidelines for Evaluation".

FDA/ICECI Compliance Manual, CPG Sec. 690.100—Direct–Fed Microbial Products, Issued May 2, 1988, Revised Mar. 1995.

Fuller, 1989, "Probiotics in Man and Animals," J. App. Bacteriol. 66:365–378.

O'Riordan et al., "Evaluation of Microencapsulation of a Bifidobacterium Strain with Starch as an Approach to Prolonging . . . ," J. App. Microbiol. 91: 1059–1066, 2001.

Schuck et al., Thermohygrometric Sensor: A tool for Optimizing the Spray Drying Process, Innov. Food Sci. Emerg. Technol. 6:45–50, 2005.

Schuck et al., "Water Activity and Glass Transition in Dairy Ingredients," Lait 85: 295–304, 2005.

Shah, "Probiotic Bacteria: Selective Enumeration and Survival in Dairy Foods", J. Dairy Sci. 83: 894–907, 2000.

Stone, 1998, "Yeast Products in the Feed Industry, a Practical Guide for Feed Professionals," Diamond V Mills, Inc., Cedar Rapids IA, 1998.

Exhibit M—Wysong Corporation, Dr. Randy L Wysong, "Rationale for Animal Nutrition" (book), First Edition 1993. Inquiry Press. Midland, MI. USA.

Exhibit Ma—Wysong Corporation, Dr. Randy L Wysong, enlarged Figure 63 from p. 83 of Exhibit M, "Rationale for Animal Nutrition."

Exhibit N—Vet–Med Health Products Inc., Dr. Randy L Wysong, "Rationale for Nature's Choice" (brochure/catalog), 1985. Midland, MI. USA.

Exhibit O—"Correlation between Phenotypic Characteristics and DNA Relatedness within *Enterococcus faecium* Strains," Teixeira et al., Journal of Clinical Microbiology, Jun. 1995.

(Continued)

*Primary Examiner*—Bruce Campell (57) ABSTRACT

A dried, ready-to-eat pet food product comprising a gelatinized starch matrix which includes a coating or filling which contains a probiotic micro-organism. The cereal product is in the form of a pet food. The product may be produced by cooking a starch source to form a gelatinized starch matrix; forming the gelatinized matrix into pieces; drying the pieces; and coating or filling the pieces with a carrier which contains probiotic micro-organisms.

OTHER PUBLICATIONS

Exhibit P—submission of information on pet food products of Wysong Medical Corporation filed with Division of Regulatory Services, State of Kentucky, Jul. 1991.

Exhibit Pa—Open Records Statutes KRS 61.870–61.884 of the State of Kentucky, Effective Jul. 1994.

Exhibit Pb—Supplemental Information on Kentucky Open Records Law, obtained at http://www.kypress.com/1stamend/open_record.asp.

Exhibit Pc—Supplemental Information on Kentucky Open Records Law, obtained at http://www.uky.edu/Regs/files/openrec/openrecs.pdf.

Exhibit Q—Wysong Corporation, product packaging bag, "Vitality Feline Diet," 4lb. bag, 1993.

Exhibit R—Wysong Corporation, excerpts from pet food product brochure, "Pet Foods and Pet Food Supplements," 1995.

Exhibit S—"Pet food and feed applications of inulin, oligofructose, and other oligosaccharides," Flickinger et al., British Journal of Nutrition (2002), 87, Suppl.2, S297–S300.

Exhibit T—"On the Presence of Inulin and Oligofructose as Natural Ingredients in the Western Diet," Van Loo et al., CRC Crit. Rev. Food Sci. Nutr., 35, 525 (1995).

Exhibit U—European Patent App. EP 0,159,891, Okonogi et al., "Granular product of dried microorganism cells and manufacturing methods therefor." Published Oct. 30, 1985.

Exhibit V—PCT International Application WO 92/12639, Casas–Perez, "Feed Additive and Method," Published Aug. 6, 1992.

Exhibit W—Japan Patent Abstract JP 57–033543, Ono et al., "Oil or fat Containing *Lactobacillus Bifidus*," Abstract only, in English, published Feb. 23, 1982.

Exhibit X—U.S. Patent No. 4,865,852, Tamatani et al., "Additive for stock feeds, stock feed containing additive, and process for preparation of additive," issued Sep. 12, 1989.

Exhibit Y—"Canine and Feline Nutrition,," Case et al., Chapter 14, "History and Regulation of Pet foods," pp. 145–152, Mosby, 1995.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2 and 6 is confirmed.

Claims 3, 4 and 8 are cancelled.

Claims 5, 7, 9-15 and 17 are determined to be patentable as amended.

Claim 16, dependent on an amended claim, is determined to be patentable.

New claims 18-22 are added and determined to be patentable.

5. A pet kibble according to claim 1 in which the probiotic micro-organism is selected from the group consisting of Bacillus coagulans, Bacillus licheniformis, Bacillus subtilis, Bifidobacterium [animalis/longum] *spp.*, [L.] *Lactobacillus johnsonii* La1, Pediococcus acidilactici, Saccharomyces cereviseae, and Enterococcus faecium SF68.

7. A dried, ready-to-eat pet food in the form of kibbles, each kibble comprising:
   a gelatinized starch matrix which includes a protein source[,]; *and*
   a coating or a filling containing a probiotic micro-organism;
   *wherein the coating or filling comprises a carrier substrate which contains the probiotic micro-organism.*

9. A pet food [product] according to claim [8] 7 in which the carrier substrate is a fat, or a protein digest, or a mixture thereof.

10. A pet food [product] according to claim 7 in which the probiotic micro-organism is selected from Bacillus coagulans, Bacillus licheniformis, Bacillus subtilis, Bifidobacterium [sp.] *spp.*, *Lactobacillus johnsonii La1*, Pediococcus acidilactici, Saccharomyces cereviseae, and Enterococcus faecium SF68.

11. A pet food [product] according to claim 7 further containing a source of soluble fiber.

12. A dried, ready-to-eat pet food in the form of coated kibbles, each kibble comprising:
   a gelatinized starch matrix which includes a protein source[,]; *and*
   a coating of a carrier substrate which contains a probiotic micro-organism; the carrier [substance] *substrate* being a fat, or a protein digest, or a mixture thereof.

13. A pet food [product] according to claim 12 in which the probiotic micro-organism is selected from Bacillus coagulans, Bacillus licheniformis, Bacillus subtilis, Bifidobacterium [sp.] *spp.*, *Lactobacillus johnsonii La1*, Pediococcus acidilactici, Saccharomyces cereviseae, and Enterococcus faecium SF68.

14. A pet food [product] according to claim 12 further containing a source of soluble fiber.

15. A process of preparing a dried, ready-to-eat pet food, the process comprising cooking a starch source and a protein source to form a gelatinized starch matrix containing protein; forming the gelatinized matrix into kibbles; drying the kibbles; and coating the kibbles with a coating *of a carrier substrate* which contains probiotic micro-organisms.

17. A dried, ready-to-eat pet food kibble comprising:
   a gelatinized starch matrix which includes a component chosen from the group consisting of inulin and fructo-oligosaccharides; *and*
   a coating *of a carrier substrate* containing a probiotic micro-organism.

*18. The pet food kibble of claim 1, wherein the probiotic micro-organism is a bacterium.*

*19. The pet food of claim 7, wherein the probiotic micro-organism is a bacterium.*

*20. The pet food of claim 12, wherein the probiotic micro-organism is a bacterium.*

*21. The process of claim 15, wherein the probiotic micro-organism is a bacterium.*

*22. The pet food kibble of claim 17, wherein the probiotic micro-organism is a bacterium.*

\* \* \* \* \*